(12) United States Patent
Yamasaki et al.

(10) Patent No.: US 9,205,104 B2
(45) Date of Patent: Dec. 8, 2015

(54) HYDROPHILIC MODIFIED POLYROTAXANE COMPOSITION

(75) Inventors: Tomoaki Yamasaki, Hyogo (JP); Shinya Okazaki, Hyogo (JP); Hiroki Okazaki, Hyogo (JP); Shigeki Hamamoto, Hyogo (JP); Changming Zhao, Chiba (JP); Minoru Iwata, Chiba (JP); Yuki Hayashi, Chiba (JP)

(73) Assignees: SUMITOMO SEIKA CHEMICALS CO., LTD., Hyogo (JP); ADVANCED SOFTMATERIALS INC., Chiba (JP)

( * ) Notice: Subject to any disclaimer, the term of this patent is extended or adjusted under 35 U.S.C. 154(b) by 65 days.

(21) Appl. No.: 14/005,137

(22) PCT Filed: Dec. 5, 2011

(86) PCT No.: PCT/JP2011/078026
§ 371 (c)(1),
(2), (4) Date: Nov. 13, 2013

(87) PCT Pub. No.: WO2012/124220
PCT Pub. Date: Sep. 20, 2012

(65) Prior Publication Data
US 2014/0066403 A1    Mar. 6, 2014

(30) Foreign Application Priority Data

| Mar. 14, 2011 | (JP) | 2011-055503 |
| Mar. 14, 2011 | (JP) | 2011-055504 |
| Oct. 31, 2011 | (JP) | 2011-239400 |

(51) Int. Cl.

| A61K 31/724 | (2006.01) |
| C08G 65/06 | (2006.01) |
| C08L 5/16 | (2006.01) |
| C08L 71/02 | (2006.01) |
| C08B 37/16 | (2006.01) |
| C08G 83/00 | (2006.01) |
| A61K 31/192 | (2006.01) |
| A61K 31/216 | (2006.01) |
| A61K 31/353 | (2006.01) |
| C08L 101/00 | (2006.01) |

(52) U.S. Cl.
CPC ............. *A61K 31/724* (2013.01); *A61K 31/192* (2013.01); *A61K 31/216* (2013.01); *A61K 31/353* (2013.01); *C08B 37/0015* (2013.01); *C08G 65/06* (2013.01); *C08G 83/007* (2013.01); *C08L 5/16* (2013.01); *C08L 71/02* (2013.01); *C08L 101/005* (2013.01)

(58) Field of Classification Search
None
See application file for complete search history.

(56) References Cited

U.S. PATENT DOCUMENTS

| 2009/0131588 A1 | 5/2009 | Ito et al. | |
| 2009/0149579 A1* | 6/2009 | Ito et al. | ............ 524/96 |

FOREIGN PATENT DOCUMENTS

| CN | 101253220 | 8/2008 |
| EP | 2123681 | 11/2009 |
| EP | 2287206 | 2/2011 |
| JP | 2007-063412 | 3/2007 |
| JP | 2007-092024 | 4/2007 |

OTHER PUBLICATIONS

Araki, J. et al "Efficient production of polyrotaxanes ..." Macromol. (2005) vol. 38, No. 17, pp. 7524-7527.*
Bors, W. et al "Chemistry of the antioxidant effect of polyphenols" Ann. NY Acad. Sci., (2002) vol. 957, pp. 57-69.*
Araki, J. et al "New solvent for polyrotaxane ..." J. Appl. Polym. Sci. (2007) vol. 105, pp. 2265-2270.*
Araki et al., "Recent advances in the preparation of cyclodextrin-based polyrotaxanes and their applications to soft materials", Soft Matter, Aug. 8, 2007, pp. 1456-1473.
Araki et al., "New Solvent for Polyrotaxane. III. Dissolution of a Poly(ethylene glycol)/Cyclodextrin Polyrotaxane in a Calcium Thiocyanate Aqueous Solution or N-Methylmorpholine-N-Oxide Monohydrate", Journal of Applied Polymer Science, vol. 105, No. 4, Jan. 1, 2007, pp. 2265-2270.

* cited by examiner

*Primary Examiner* — Leigh Maier
(74) *Attorney, Agent, or Firm* — Hamre, Schumann, Mueller & Larson, P.C.

(57) ABSTRACT

The present invention aims to provide a hydrophilic modified polyrotaxane composition having excellent storage stability. The present invention relates to a hydrophilic modified polyrotaxane composition comprising: a hydrophilic modified polyrotaxane produced by modifying, with hydrophilic modifying groups, all or part of hydroxy groups on a cyclodextrin of a polyrotaxane containing the cyclodextrin, a polyethylene glycol which is included in the cavities of the cyclodextrin molecules in a skewered manner, and a capping group that is placed at each end of the polyethylene glycol and prevents dissociation of the cyclodextrin molecules from the polyethylene glycol; and a polyphenol antioxidant.

6 Claims, 1 Drawing Sheet

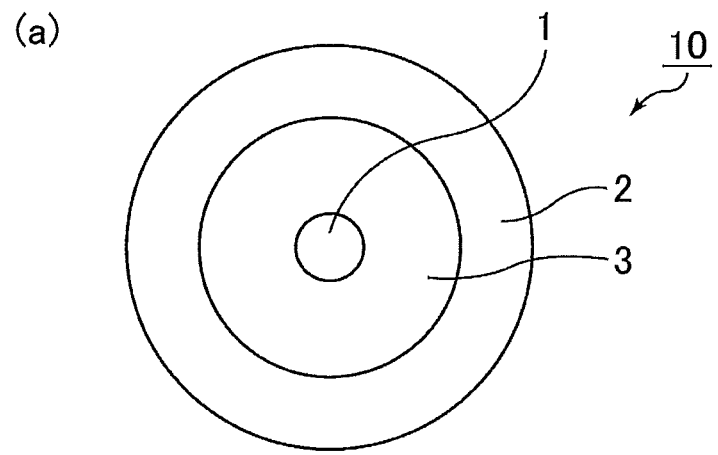
(a)
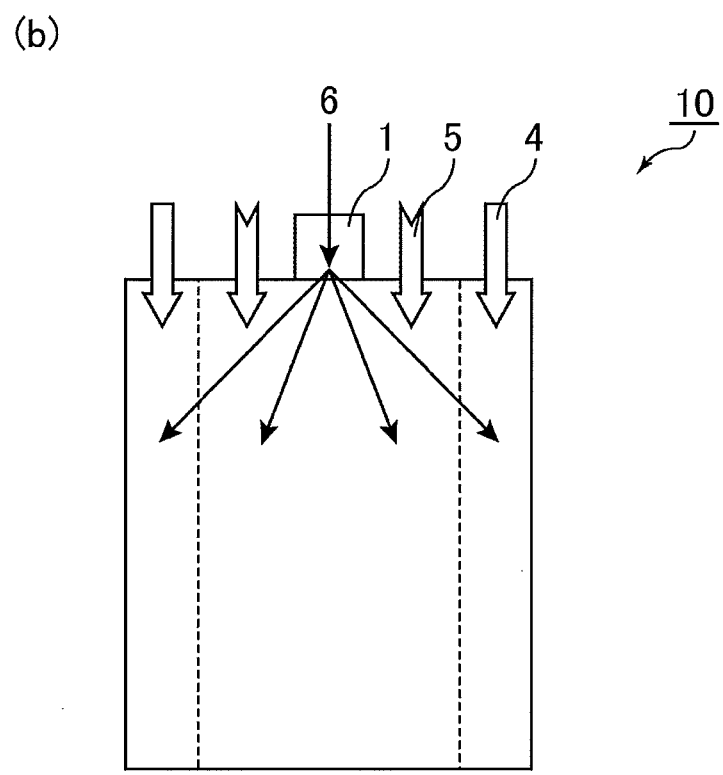
(b)

HYDROPHILIC MODIFIED POLYROTAXANE COMPOSITION

TECHNICAL FIELD

The present invention relates to a hydrophilic modified polyrotaxane composition.

BACKGROUND ART

"Slide-ring gels", new gels different from physical gels and chemical gels, have been developed in recent years. A compound that is used for such slide-ring gels and is drawing attention is a crosslinked polyrotaxane.

Crosslinked polyrotaxanes are produced by crosslinking polyrotaxanes in which a capping group is introduced at each end of a pseudopolyrotaxane. In the case that a pseudopolyrotaxane is formed from a polyethylene glycol (hereinafter, also referred to as a "PEG") having a reactive group at each end and a cyclodextrin that includes the PEG, for example, the resulting crosslinked polyrotaxane has a structure in which linear molecules of the PEG are threaded through cyclodextrin molecules in a skewered manner and the cyclodextrin molecules are movable along the linear molecules (has a pulley effect). The pulley effect allows the crosslinked polyrotaxane to uniformly distribute tensile force applied thereto. The crosslinked polyrotaxane is therefore not likely to have cracks or flaws, i.e., has excellent characteristics that conventional crosslinked polymers do not have.

Polyrotaxanes used for production of a crosslinked polyrotaxane typically contain isolated cyclodextrin molecules (hereinafter also referred to as "free cyclodextrin molecules"). These free cyclodextrin molecules deteriorate the characteristics of a crosslinked polyrotaxane. Hence, polyrotaxanes need to be purified by a method such as reprecipitation such that free cyclodextrin molecules are removed.

Patent Literature 1 describes a method for producing a hydrophilic modified polyrotaxane which includes mixing a carboxylated polyethylene glycol and a cyclodextrin molecules to obtain a pseudopolyrotaxane with a carboxylated polyethylene glycol included in the cavities of the cyclodextrin molecules in a skewered manner, capping each end of the pseudopolyrotaxane with a capping group, and modifying all or part of hydroxy groups on the cyclodextrin with hydrophilic modifying groups.

In the production method described in Patent Literature 1, the aqueous solution of the obtained hydrophilic modified polyrotaxane is purified by dialysis using a dialysis tube, whereby free cyclodextrin molecules with all or part of hydroxy groups modified with hydrophilic modifying groups (hereinafter also referred to as "modified cyclodextrin molecules") which deteriorate the characteristics of a crosslinked polyrotaxane are removed.

CITATION LIST

Patent Literature

Patent Literature 1: JP 2007-63412 A (Japanese Kokai Publication No 2007-63412)

SUMMARY OF INVENTION

Technical Problem

Such a hydrophilic modified polyrotaxane from which modified cyclodextrin molecules are removed is suitable for a raw material of a crosslinked polyrotaxane right after the production. The hydrophilic modified polyrotaxane, however, may be decomposed with time during storage to release modified cyclodextrin molecules.

A hydrophilic modified polyrotaxane which has released modified cyclodextrin molecules during storage deteriorates the characteristics of a crosslinked polyrotaxane when used as a raw material of the crosslinked polyrotaxane, even if modified cyclodextrin molecules are removed in production of the hydrophilic modified polyrotaxane. The hydrophilic modified polyrotaxane therefore may need to be purified again before it is used as a raw material of a crosslinked polyrotaxane to effectively achieve the characteristics of a crosslinked polyrotaxane, which complicates the production process. Accordingly, a hydrophilic modified polyrotaxane having excellent storage stability where isolation of modified cyclodextrin molecules is prevented has been desired.

The present invention aims to provide a hydrophilic modified polyrotaxane composition having excellent storage stability to solve the above problem.

Solution to Problem

The present invention relates to a hydrophilic modified polyrotaxane composition comprising: a hydrophilic modified polyrotaxane produced by modifying, with hydrophilic modifying groups, all or part of hydroxy groups on a cyclodextrin of a polyrotaxane containing the cyclodextrin, a polyethylene glycol which is included in the cavities of the cyclodextrin molecules in a skewered manner, and a capping group that is placed at each end of the polyethylene glycol and prevents dissociation of the cyclodextrin molecules from the polyethylene glycol; and a polyphenol antioxidant.

The present invention is described in detail below.

The present inventors have found that adding a polyphenol antioxidant to a hydrophilic modified polyrotaxane enables production of a hydrophilic modified polyrotaxane composition having excellent storage stability where isolation of modified cyclodextrin molecules is less likely to occur during storage. Thereby, the present invention has been completed.

The hydrophilic modified polyrotaxane composition of the present invention includes a hydrophilic modified polyrotaxane produced by modifying, with hydrophilic modifying groups, all or part of hydroxy groups on a cyclodextrin of a polyrotaxane containing the cyclodextrin, a polyethylene glycol which is included in the cavities of the cyclodextrin molecules in a skewered manner, and a capping group that is placed at each end of the polyethylene glycol and prevents dissociation of the cyclodextrin molecules from the polyethylene glycol.

A hydrophilic modified polyrotaxane is typically obtainable by mixing a cyclodextrin and a PEG to produce a pseudopolyrotaxane which has the PEG included in the cavities of the cyclodextrin molecules in a skewered manner, placing a capping group at each end of a pseudopolyrotaxanes to prevent dissociation of the skewered cyclodextrin molecules, and modifying all or part of hydroxy groups on the cyclodextrin with hydrophilic modifying groups.

The PEG in the hydrophilic modified polyrotaxane composition of the present invention preferably has a weight average molecular weight of 1,000 to 500,000, more preferably 10,000 to 300,000, and still more preferably 10,000 to 100,000. A weight average molecular weight of the PEG of less than 1,000 may result in poor characteristics of the resulting crosslinked polyrotaxane. A weight average molecular weight of the PEG of more than 500,000 may give reduced storage stability to a hydrophilic modified polyrotaxane.

The weight average molecular weight herein is a PEG equivalent value calculated through measurement by gel permeation chromatography (GPC). A column used for determination of a PEG-equivalent weight average molecular weight by GPC is, for example, TSKgel SuperAWM-H (product of TOSOH CORPORATION).

The PEG preferably has a reactive group at each end. The reactive group can be introduced at each end of the PEG by a conventionally known method.

The reactive group introduced at each end of the PEG can be appropriately changed depending on the capping group to be used. Examples of the reactive group include, but not particularly limited to, hydroxy groups, amino groups, carboxyl groups, and thiol groups. Particularly, carboxyl groups are preferred. Examples of the method for introducing a carboxyl group at each end of the PEG include a method which oxidizes each end of the PEG using TEMPO (2,2,6,6-tetramethyl-1-piperidinyloxy radicals) and sodium hypochlorite.

Examples of the cyclodextrin include α-cyclodextrin, β-cyclodextrin, γ-cyclodextrin, and derivatives of these cyclodextrins. Among these, at least one selected from the group consisting of α-cyclodextrin, β-cyclodextrin, and γ-cyclodextrin is preferred, and α-cyclodextrin is more preferred in terms of the inclusion property. These cyclodextrins may be used alone or in combination.

The hydrophilic modifying groups are not particularly limited. Still, specifically, the hydrophilic modifying groups are preferably at least one selected from the group consisting of carboxyl groups, sulfonic groups, sulfuric acid ester groups, phosphoric acid ester groups, amino groups, quaternary ammonium bases, and hydroxy alkyl groups, and more preferably hydroxy alkyl groups resulting from a reaction with a compound such as propylene oxide, in view of the diversity of the reaction in synthesis of a crosslinked polyrotaxane.

The inclusion ratio of the hydrophilic modified polyrotaxane is preferably 6 to 60%, although it depends on the use and purpose of the polyrotaxane. An inclusion ratio of the hydrophilic modified polyrotaxane of lower than 6% may not give a sufficient pulley effect to the resulting crosslinked polyrotaxane. An inclusion ratio of the hydrophilic modified polyrotaxane of higher than 60% may result in too dense arrangement of cyclodextrin molecules, which are cyclic molecules, so that the mobility of the cyclodextrin molecules decreases. In order to give appropriate mobility to the cyclodextrin molecules and give a favorable pulley effect to the resulting crosslinked polyrotaxane, the inclusion ratio of the hydrophilic modified polyrotaxane is more preferably 15 to 40%, and still more preferably 20 to 30%.

The "inclusion ratio" herein refers to a ratio of the inclusion amount of cyclodextrin molecules including a PEG to the maximum inclusion amount of cyclodextrin molecules for the PEG. The inclusion ratio is optionally controllable by changing the mixing ratio of the PEG to the cyclodextrin or the kind of aqueous medium. The maximum inclusion amount refers to the number of cyclodextrin molecules in the case of the close-packed inclusion state in which one cyclodextrin molecule includes two repeating units of the PEG.

The inclusion ratio of the hydrophilic modified polyrotaxane can be measured by $^1$H-NMR. Specifically, the inclusion ratio can be calculated by dissolving the obtained polyrotaxane in DMSO-$d_6$, subjecting the solution to measurement using an NMR measuring device (product of Varian Technologies Japan Ltd., "VARIAN Mercury-400BB"), and comparing the integrated value of cyclodextrin at 4 to 6 ppm and the integrated value of cyclodextrin and PEG at 3 to 4 ppm. Since a hydrophilic modified polyrotaxane is obtained by modifying hydroxy group (s) on the cyclodextrin of the polyrotaxane with hydrophilic modifying group(s), the inclusion ratio thereof is the same as the inclusion ratio of the polyrotaxane.

Examples of the polyphenol antioxidant in the hydrophilic modified polyrotaxane composition of the present invention include catechin, epicatechin, gallocatechin, catechin gallate, epicatechin gallate, gallocatechin gallate, epigallocatechin gallate, epigallocatechin, tannic acid, gallotannin, ellagitannin, caffeic acid, dihydrocaffeic acid, chlorogenic acid, isochlorogenic acid, gentisic acid, homogentisic acid, gallic acid, ellagic acid, rosmarinic acid, rutin, quercetin, quercetagin, quercetagetin, gossypetin, anthocyanin, leucoanthocyanin, proanthocyanidin, and enocyanin. For further stabilization of a long-term storage stability, more preferred among these is at least one selected from the group consisting of rosmarinic acid, gallic acid, catechin, epicatechin, epigallocatechin, epicatechin gallate, and epigallocatechin gallate.

These polyphenol antioxidants may be used alone or in combination.

Also, the polyphenol antioxidant is a natural compound widely contained in plants, and thus has a preferred characteristic that it is highly safe for human bodies. Hence, the hydrophilic modified polyrotaxane composition of the present invention, containing a polyphenol antioxidant as an antioxidant, not only has high storage stability but also enables the resulting crosslinked polyrotaxane to be used as a material having excellent quality stability and safety in uses such as cosmetics and biomaterials which directly affect human bodies. Polyphenol antioxidants also have an excellent antibacterial effect, and thus are expected to have an antibacterial effect on a final product to which the crosslinked polyrotaxane is applied.

The hydrophilic modified polyrotaxane composition of the present invention contains the polyphenol antioxidant in an amount of 0.001 to 5% by weight, more preferably 0.005 to 2% by weight, and still more preferably 0.01 to 1% by weight, based on the hydrophilic modified polyrotaxane. An amount of the polyphenol antioxidant of less than 0.001% by weight may not improve the storage stability. An amount of the polyphenol antioxidant of more than 5% by weight may not achieve any better effect of increasing the amount, which is not economical.

The method for preparing a hydrophilic modified polyrotaxane composition of the present invention is not particularly limited. Still, since a hydrophilic modified polyrotaxane and a polyphenol antioxidant need to be uniformly mixed in production of a dry, solid hydrophilic modified polyrotaxane composition, a method is preferred which includes putting a hydrophilic modified polyrotaxane and a polyphenol antioxidant into a solvent, mixing them with stirring to prepare a mixture containing the hydrophilic modified polyrotaxane, the polyphenol antioxidant, and the solvent, and drying the mixture, for producing a hydrophilic modified polyrotaxane composition having excellent storage stability. For producing a hydrophilic modified polyrotaxane composition having even better storage stability, a method is more preferred which includes drying a mixture containing a solvent in which at least one of a hydrophilic modified polyrotaxane and a polyphenol antioxidant is dissolved in the solvent.

In the preparation of a mixture containing a hydrophilic modified polyrotaxane, a polyphenol antioxidant, and a solvent, the solvent for dissolving at least the hydrophilic modified polyrotaxane may be, for example, an alcohol such as isopropyl alcohol, butyl alcohol, or ethylene glycol, an ether ester such as cellosolve acetate, butyl cellosolve acetate, or diethylene glycol monoethyl ether, a glycol ether such as ethylene glycol monoethyl ether, ethylene glycol monobutyl ether, or propylene glycol monomethyl ether, or water.

In the preparation of a mixture containing a hydrophilic modified polyrotaxane, a polyphenol antioxidant, and a solvent, if the polyphenol antioxidant is not dissolved in the solvent, mixing these in the form of fine particles before the preparation of the mixture allows production of a hydrophilic modified polyrotaxane composition having better storage stability. The method for making the polyphenol antioxidant into fine particles may be a known method such as mechanical grinding using a grinder (e.g. ball mill, pin mill), or particle size reduction through crystallization.

In the case of making the polyphenol antioxidant into fine particles, the volume-average particle size of the polyphenol antioxidant is preferably 0.01 to 100 μm, more preferably 0.1 to 30 μm, and still more preferably 0.1 to 10 μm. A volume-average particle size of the polyphenol antioxidant of smaller than 0.01 μm may not allow the polyphenol antioxidant to be easily treated by grinding or crystallization, and may not further improve the storage stability either. A volume-average particle size of the polyphenol antioxidant of greater than 100 μm may not allow the polyphenol antioxidant to be uniformly dispersed in the resulting hydrophilic modified polyrotaxane composition, which may decrease the effect of improving the storage stability.

The volume-average particle size of the polyphenol antioxidant can be measured by a laser diffraction particle size analyzer.

The present inventors have found that the decomposition with time of the obtained hydrophilic modified polyrotaxane composition during storage can be more effectively suppressed by a method of spraying the mixture containing a hydrophilic modified polyrotaxane, a polyphenol antioxidant, and a solvent into heated gas stream for drying, or by a method of forming the mixture into a thin film state for drying.

These drying methods require short exposure time to heat and do not excessively increase the temperature of the product during the drying, and thus suppress generation of radicals inducing decomposition of the hydrophilic modified polyrotaxane during the drying. Hence, the polyphenol antioxidant added is not consumed during the drying, and a hydrophilic modified polyrotaxane composition having better storage stability can be obtained.

In the case of spray-drying the mixture containing a hydrophilic modified polyrotaxane, a polyphenol antioxidant, and a solvent, the method for spraying the mixture may be, for example, a nozzle method using a nozzle such as a pressure nozzle, a two-fluid nozzle, a four-fluid nozzle, or an ultrasonic nozzle, or a rotating disk method.

The nozzle method is suitable for the case that the mixture containing a hydrophilic modified polyrotaxane, a polyphenol antioxidant, and a solvent has low viscosity. Examples of the spray dryer usable for the nozzle method include a nozzle atomizer spray dryer. The method employed in those nozzle atomizer spray dryers is roughly classified into counter spraying of spraying the mixture against the hot-gas blowing direction, and parallel spraying of spraying the mixture in the same direction as the hot-gas blowing direction. The counter spraying leads to long residence time of the sprayed mixture, while the parallel spraying leads to short residence time of the sprayed mixture.

The rotating disc method is suitable for the case that the mixture has high viscosity.

Examples of the spray dryer used for the rotating disc method include a rotary atomizer spray dryer.

In the drying of the mixture containing a hydrophilic modified polyrotaxane, a polyphenol antioxidant, and a solvent, the gas-stream may include a gas such as air or nitrogen.

In the drying, the inlet temperature of the spray dryer is preferably 70 to 200° C., and the outlet temperature is preferably 50 to 110° C.

An inlet temperature of the spray dryer of lower than 70° C. may lead to insufficient drying. An inlet temperature of the spray dryer of higher than 200° C. may decompose the hydrophilic modified polyrotaxane during the drying to decrease the inclusion ratio. Here, even if an undecomposed hydrophilic modified polyrotaxane is obtained, it may be decomposed with time during storage, eventually releasing the modified cyclodextrin molecules. The inlet temperature of the spay dryer is more preferably 70 to 180° C., and still more preferably 70 to 170° C.

An outlet temperature of the spray dryer of lower than 50° C. may lead to insufficient drying. An outlet temperature of the spray dryer of higher than 110° C. may decompose the hydrophilic modified polyrotaxane to decrease the inclusion ratio. Here, even if an undecomposed hydrophilic modified polyrotaxane is obtained, it may be decomposed with time during storage, eventually releasing the modified cyclodextrin molecules. The outlet temperature of the spray dryer is more preferably 60 to 100° C., and still more preferably 70 to 100° C.

In the drying of the mixture, the inlet temperature may be controlled by blowing out at least two different temperature hot gases from the inlet of the spray dryer. For example, in the case of blowing out two different temperature hot gasses, the inlet temperature of the spray dryer can be controlled by changing the flow ratio of the two different temperature hot gasses.

The inlet temperature is conveniently computable by the following formula.

$$\text{Inlet temperature} = (\text{temperature of higher temperature hot gas} \times (\text{flow rate of higher temperature hot gas} / \text{total flow rate of hot gases})) + (\text{temperature of lower temperature hot gas} \times (\text{flow rate of lower temperature hot gas} / \text{total flow rate of hot gases}))$$

In spraying of the mixture containing a hydrophilic modified polyrotaxane, a polyphenol antioxidant, and a solvent from the spray dryer, the mixture is preferably sprayed into a first higher temperature hot gas, and the resulting mostly dried hydrophilic modified polyrotaxane composition particles are then brought into contact with a second lower temperature hot gas for further drying.

FIG. 1 illustrates an example in which at least two different temperature hot gasses are blown out from a spray dryer inlet. FIG. 1(a) is a schematic top view of the inlet of the spray dryer. FIG. 1(b) is a schematic side view of the inlet of the spray dryer. As illustrated in FIG. 1, an inlet 10 of the spray dryer is cylindrical and has a spray nozzle 1 disposed at the center of the circle at the top of the cylinder.

A mixture 6 containing a hydrophilic modified polyrotaxane, a polyphenol antioxidant, and a solvent is sprayed in a conical pattern from a spraying nozzle 1. At this time, for drying, a higher temperature hot gas is blown out from the center portion (a higher temperature hot gas blowing portion 3) of the inlet cylinder in a higher temperature hot gas blowing direction 5, and a lower temperature hot gas is blown out from the peripheral portion (a lower temperature hot gas blowing portion 2) in a lower temperature hot gas blowing direction 4.

The pressure in the dryer system in the drying is not particularly limited, but is typically a pressure near an atmospheric pressure. Vacuum drying is also possible, and drying under a pressure not higher than an atmospheric pressure is preferred.

The residence time of the sprayed mixture containing a hydrophilic modified polyrotaxane, a polyphenol antioxidant, and a solvent is typically several seconds to several minutes, and for suppression of isolation of modified cyclodextrin molecules, it is preferably three minutes or shorter, and more preferably two minutes or shorter. Too short a residence time of the sprayed mixture containing a hydrophilic modified polyrotaxane, a polyphenol antioxidant, and a solvent results in insufficient drying.

The diameter of the drops of the mixture containing a hydrophilic modified polyrotaxane, a polyphenol antioxidant, and a solvent to be sprayed is preferably 1 to 2,000 µm, and more preferably 5 to 500 µm. A diameter of the drops of smaller than 1 µm may cause the drops to be blown together with the gas, decreasing the drying yield. A diameter of the drops of larger than 2,000 µm may lead to a small total surface area of the whole drops, decreasing the drying speed.

In the case of drying the mixture containing a hydrophilic modified polyrotaxane, a polyphenol antioxidant, and a solvent in a thin film state, the method for making the mixture into a thin film state may be, for example, spray coating, spin coating, or dip coating.

When the mixture is made into a thin film state, the thickness of the mixture in a thin film state is preferably 0.1 to 2 mm, more preferably 0.1 to 1 mm, and still more preferably 0.1 to 0.5 mm. A thickness of the mixture in a thin film state of smaller than 0.1 mm may decrease the yield per hour, which is not economical. A thickness of the mixture in a thin film state of larger than 2 mm may result in insufficient drying.

The method for controlling the thickness of the mixture in a thin film state depends on factors such as the type of dryer to be used. In the case of the drum dryer mentioned later, for example, the thickness may be appropriately controlled by changing conditions such as the drum interval, the drum rotation speed, and the feeding speed of the mixture.

Examples of the dryer used for drying the mixture in a thin film state include drum dryers and centrifugal thin film dryers. Especially, a drum dryer is preferred because the structure of the device is comparatively simple and easy to maintain.

In the case of a drum dryer, for example, the mixture is applied to the surface of a heated drum to a thin film state, and then promptly evaporated to dryness. The dried product is continuously scraped with a fixedly mounted knife while the drum makes one rotation, so that a hydrophilic modified polyrotaxane composition is obtained.

The drying temperature in the drying of the mixture in a thin film state is preferably 70 to 200° C., more preferably 90 to 180° C., and still more preferably 100 to 170° C. A drying temperature of lower than 70° C. may lead to insufficient drying. A drying temperature of higher than 200° C. may decompose the hydrophilic modified polyrotaxane to decrease the inclusion ratio.

The pressure in the dryer system in the drying of the mixture in a thin film state is not particularly limited, but is typically a pressure near an atmospheric pressure. Vacuum drying is also possible, and drying under a pressure not higher than an atmospheric pressure is preferred.

The drying time of the mixture in a thin film state is typically several seconds to several minutes. For suppression of isolation of modified cyclodextrin molecules, it is preferably ten minutes or shorter, more preferably five minutes or shorter, and still more preferably two minutes or shorter. Too short a drying time of the mixture in a thin film state leads to insufficient drying.

Advantageous Effects of Invention

The present invention can provide a hydrophilic modified polyrotaxane composition having excellent storage stability.

BRIEF DESCRIPTION OF DRAWINGS

FIG. 1(a) is a schematic top view of the inlet of the spray dryer, and FIG. 1(b) is a schematic side view of the inlet of the spray dryer, both in the case of, for example, blowing out at least two different temperature hot gasses from the inlet of the spray dryer in the drying in the present invention.

DESCRIPTION OF EMBODIMENTS

The present invention is described below in more detail based on examples which, however, are not intended to limit the scope of the present invention. In the following, a PEG having a carboxyl group at each end was produced by oxidation of a PEG in accordance with the method described in WO 05/052026 A.

Example 1

(1) Preparation of PEG Having Carboxyl Group at Each End by TEMPO Oxidation of PEG A 20-L reaction vessel was charged with 10 L of water, and 1 kg of a PEG (molecular weight: 35,000), 10 g of TEMPO (2,2,6,6-tetramethyl-1-piperidinyloxy radicals), and 100 g of sodium bromide were dissolved. To the solution was added 500 mL of a commercially available aqueous solution of sodium hypochlorite (effective chlorine concentration: 5% by weight), and the resulting mixture was stirred at room temperature for 30 minutes. An amount of 500 mL of ethanol was added to decompose an excess of the sodium hypochlorite to terminate the reaction. Liquid separation extraction using 5 L of methylene chloride was performed three times to extract components other than the mineral salt. The methylene chloride was removed by vacuum distillation. Thereby, 1 kg of a PEG having a carboxyl group at each end was obtained.

(2) Preparation of Aqueous Dispersion of Pseudopolyrotaxane from α-Cyclodextrin and PEG Having Carboxyl Group at Each End The prepared 1 kg of the PEG having a carboxyl group at each end was mixed with 35 L of water, and further with 4 kg of α-cyclodextrin. The resulting mixture was heated to 70° C. for dissolution. The solution was cooled to 4° C. with stirring, thereby a milky dispersion of a pseudopolyrotaxane was precipitated.

(3) Drying of Aqueous Dispersion of Pseudopolyrotaxane

The prepared dispersion of a pseudopolyrotaxane in an amount of 40 kg was dried by a spray dryer, so that 4.7 kg of a powdery dry product was produced. The inlet temperature of the dryer was 165° C., and the outlet temperature was 90° C.

(4) Preparation of Polyrotaxane

In a 50-L flask, 45 g of adamantanamine was dissolved in 17 L of dimethyl formamide (DMF) at room temperature.

Then, the 4.7 kg of the obtained pseudopolyrotaxane was added to the flask, and the flask was promptly shaken well.

Subsequently, a solution of 130 g of a BOP reagent (benzotriazol-1-yl-oxy-tris(dimethylamino)phosphonium hexafluorophosphate) in 8 L of DMF was added to the flask, and the flask was promptly shaken well.

Furthermore, to the flask was added a solution of 50 mL of diisopropylethylamine in 8 L of DMF, and the obtained mixture was stirred overnight at normal temperature.

The obtained mixture was filtered. The resulting residue was mixed with 30 kg of water. The mixture was heated to 70° C. with stirring, stirred for 60 minutes at the same temperature, and filtered again. The obtained residue was vacuum-dried for 16 hours at 60° C. using a vacuum dryer, whereby 3 kg of a polyrotaxane was obtained.

(5) Hydroxypropylation of Hydroxy Group on Cyclodextrin

In a 50-L reaction vessel, 18 L of water, 1 kg of sodium hydroxide, and 3 kg of the obtained polyrotaxane were dissolved. An amount of 6 kg of propylene oxide was added, and the resulting mixture was stirred overnight at room temperature under nitrogen atmosphere. The mixture was neutralized with a 1 mol/L aqueous solution of HCl, purified, and concentrated, whereby 60 kg of an aqueous solution of a hydrophilic modified polyrotaxane with a solids concentration of 5% was obtained.

(6) Preparation of Mixture

To the obtained aqueous solution of a hydrophilic modified polyrotaxane was added a rosmarinic acid (rosemary extract, product of Mitsubishi-Kagaku Foods Corporation, "RM-21A base") in an amount of 0.3 g (0.01% by weight, based on the hydrophilic modified polyrotaxane) as a polyphenol antioxidant, so that a mixture containing a hydrophilic modified polyrotaxane, rosmarinic acid, and water was obtained.

(7) Drying of Mixture

A 170° C. hot gas was blown out from the inlet of a nozzle atomizer spray dryer (product of OHKAWARA KAKOHKI Co., LTD.), so that 60 kg of the mixture obtained in "(6) Preparation of mixture" was spray-dried at an inlet temperature of 170° C. and an outlet temperature of 100° C. Thereby, 3 kg of a hydrophilic modified polyrotaxane composition was obtained. The obtained hydrophilic modified polyrotaxane composition was subjected to measurement with a high-performance liquid chromatograph (product of Waters, "Alliance 2695"), and no modified cyclodextrin molecules were detected.

Example 2

An amount of 3 kg of a hydrophilic modified polyrotaxane composition was obtained in the same manner as in Example 1, except that the amount of the rosmarinic acid (rosemary extract, product of Mitsubishi-Kagaku Foods Corporation, "RM-21A base") added in "(6) Preparation of mixture" was changed to 1.5 g (0.05% by weight, based on the hydrophilic modified polyrotaxane). The obtained hydrophilic modified polyrotaxane composition was subjected to measurement as in Example 1, and no modified cyclodextrin molecules were detected.

Example 3

An amount of 3 kg of a hydrophilic modified polyrotaxane composition was obtained in the same manner as in Example 1, except that in "(6) Preparation of mixture", gallic acid in an amount of 3 g (0.1% by weight, based on the hydrophilic modified polyrotaxane) was added as a polyphenol antioxidant in place of the 0.3 g of rosmarinic acid. The obtained hydrophilic modified polyrotaxane composition was subjected to measurement as in Example 1, and no modified cyclodextrin molecules were detected.

Example 4

An amount of 3 kg of a hydrophilic modified polyrotaxane composition was obtained in the same manner as in Example 1, except that in "(6) Preparation of mixture", a tea extract with a catechin content of 5% (product of JAPAN CHLOROPHYLL Co., Ltd., "CATEKING S") in an amount of 60 g (0.1% by weight, based on the hydrophilic modified polyrotaxane) was used as a polyphenol antioxidant in place of the 0.3 g of rosmarinic acid. The obtained hydrophilic modified polyrotaxane composition was subjected to measurement as in Example 1, and no modified cyclodextrin molecules were detected.

Example 5

A hydrophilic modified polyrotaxane composition was obtained in the same manner as in Example 1, except that in "(7) Drying of mixture", a 190° C. hot gas and a 120° C. hot gas were blown out from the inlet of the nozzle atomizer spray dryer in the same manner as in FIG. 1, with an inlet temperature of 170° C. and an outlet temperature of 100° C. The obtained hydrophilic modified polyrotaxane composition was subjected to measurement as in Example 1, and no modified cyclodextrin molecules were detected.

Example 6

A hydrophilic modified polyrotaxane composition was obtained in the same manner as in Example 1, except that in "(7) Drying of mixture", the drying was performed using a double-drum type drum dryer (product of KATSURAGI INDUSTRY CO., LTD., "D-0303 type") with a drum surface temperature of 120° C. and a number of drum rotations of 1 rpm (drying time: 40 seconds) in place of a nozzle atomizer spray dryer. The thickness of the film of the mixture adhered to the drum in the drying was 0.5 mm. The obtained hydrophilic modified polyrotaxane composition was subjected to measurement as in Example 1, and no modified cyclodextrin molecules were detected.

Comparative Example 1

A hydrophilic modified polyrotaxane was obtained in the same manner as in Example 1, except that rosmarinic acid was not used in "(6) Preparation of mixture". The measurement was performed in the same manner as in Example 1, which showed that the obtained hydrophilic modified polyrotaxane had a cyclodextrin content of 0.1% by weight.

Comparative Example 2

A hydrophilic modified polyrotaxane was obtained in the same manner as in Example 5, except that rosmarinic acid was not used in "(6) Preparation of mixture". The obtained hydrophilic modified polyrotaxane was subjected to measurement as in Example 1, and no modified cyclodextrin molecules were detected.

Comparative Example 3

A hydrophilic modified polyrotaxane was obtained in the same manner as in Example 6, except that rosmarinic acid was not used in "(6) Preparation of mixture". The obtained hydrophilic modified polyrotaxane was subjected to measurement as in Example 1, and no modified cyclodextrin molecules were detected.

<Evaluation>

The hydrophilic modified polyrotaxane compositions obtained in the examples and the hydrophilic modified polyrotaxanes obtained in the comparative examples were stored in a 40° C. thermostatic bath. The modified cyclodextrin content of each of these products was measured on the 30th and 120th days using a high-performance chromatograph (product of Waters, "Alliance 2695"). The results are shown in Table 1 together with the values immediately after the production.

TABLE 1

| | Polyphenol antioxidant | | Drying method | | Modified cyclodextrin content (% by weight) | | |
|---|---|---|---|---|---|---|---|
| | Kind | Amount (% by weight) | Drying process | Temperature (° C.) | Day 0 | Day 30 | Day 120 |
| Example 1 | Rosmarinic acid | 0.01 | Spraying (1 hot gas) | Inlet/outlet = 170/100 | Not detected | Not detected | 1 |
| Example 2 | Rosmarinic acid | 0.05 | Spraying (1 hot gas) | Inlet/outlet = 170/100 | Not detected | Not detected | Not detected |
| Example 3 | Gallic acid | 0.1 | Spraying (1 hot gas) | Inlet/outlet = 170/100 | Not detected | Not detected | 0.1 |
| Example 4 | Catechin | 0.1 | Spraying (1 hot gas) | Inlet/outlet = 170/100 | Not detected | Not detected | 0.1 |
| Example 5 | Rosmarinic acid | 0.01 | Spraying (2 hot gasses) | Inlet/outlet = 170/100 | Not detected | Not detected | Not detected |
| Example 6 | Rosmarinic acid | 0.01 | Thin film | 120 | Not detected | 0.4 | 0.8 |
| Comparative Example 1 | — | — | Spraying (1 hot gas) | Inlet/outlet = 170/100 | 0.1 | 3 | 9 |
| Comparative Example 2 | — | — | Spraying (2 hot gasses) | Inlet/outlet = 170/100 | Not detected | 2 | 4 |
| Comparative Example 3 | — | — | Thin film | 120 | Not detected | 2 | 5 |

INDUSTRIAL APPLICABILITY

The present invention can provide a hydrophilic modified polyrotaxane composition having excellent storage stability.

REFERENCE SIGNS LIST

1 Spray nozzle for hydrophilic modified polyrotaxane solution
2 Lower temperature hot gas blowing portion
3 Higher temperature hot gas blowing portion
4 Lower temperature hot gas blowing direction
5 Higher temperature hot gas blowing direction
6 Mixture containing hydrophilic modified polyrotaxane solution
10 Inlet of spray dryer

The invention claimed is:

1. A hydrophilic modified polyrotaxane composition comprising:
   a hydrophilic modified polyrotaxane produced by modifying, with hydrophilic modifying groups, all or part of hydroxy groups on a cyclodextrin of a polyrotaxane containing the cyclodextrin,
      wherein a polyethylene glycol is included in cavities of molecules of the cyclodextrin in a skewered manner, and
      a capping group is placed at each end of the polyethylene glycol and prevents dissociation of the molecules of the cyclodextrin from the polyethylene glycol; and
   a polyphenol antioxidant in an amount range from 0.001 to 0.1% by weight relative to the hydrophilic modified polyrotaxane.

2. The hydrophilic modified polyrotaxane composition according to claim 1,
   wherein the polyethylene glycol has a weight average molecular weight in a range from 1,000 to 500,000.

3. The hydrophilic modified polyrotaxane composition according to claim 1,
   wherein the cyclodextrin is at least one material selected from the group consisting of α-cyclodextrin, β-cyclodextrin, and γ-cyclodextrin.

4. The hydrophilic modified polyrotaxane composition according to claim 1,
   which comprises the polyrotaxane at an inclusion ratio in a range from 6 to 60%.

5. The hydrophilic modified polyrotaxane composition according to claim 1,
   wherein the hydrophilic modifying groups are at least one group selected from the group consisting of carboxyl groups, sulfonic groups, sulfuric acid ester groups, phosphoric acid ester groups, amino groups, quaternary ammonium bases, and hydroxy alkyl groups.

6. The hydrophilic modified polyrotaxane composition according to claim 1,
   wherein the polyphenol antioxidant is at least one material selected from the group consisting of rosmarinic acid, gallic acid, catechin, epicatechin, epigallocatechin, epicatechin gallate, and epigallocatechin gallate.

* * * * *